(12) United States Patent
Kullik et al.

(10) Patent No.: US 8,814,806 B2
(45) Date of Patent: Aug. 26, 2014

(54) DEVICE FOR DETERMINING A CONDITION OF FLOW IN A RESPIRATION SYSTEM

(75) Inventors: Götz Kullik, Lübeck (DE);
Hans-Ullrich Hansmann, Barnitz (DE);
Dieter Settgast, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 900 days.

(21) Appl. No.: 12/469,907

(22) Filed: May 21, 2009

(65) Prior Publication Data

US 2009/0312661 A1 Dec. 17, 2009

(30) Foreign Application Priority Data

Jun. 17, 2008 (DE) .......................... 10 2008 028 733

(51) Int. Cl.
*A61B 5/087* (2006.01)
*A61B 5/097* (2006.01)
*A61M 16/20* (2006.01)

(52) U.S. Cl.
USPC .................. 600/538; 128/205.23; 128/205.24

(58) Field of Classification Search
CPC ...... A61B 5/0876; A61B 5/085; A61B 5/097; A61B 5/0873; A61M 16/208; A61M 2016/003; A61M 2106/0033; A61M 2016/0039; A61M 2016/0021; A61M 2016/0027; A61M 2205/3317
See application file for complete search history.

(56) References Cited

U.S. PATENT DOCUMENTS

| | | | | |
|---|---|---|---|---|
| 876,147 | A * | 1/1908 | Cadman | 137/329.03 |
| 2,770,231 | A * | 11/1956 | Falk | 128/205.18 |
| 4,227,547 | A * | 10/1980 | Cameron | 137/554 |
| 4,633,868 | A * | 1/1987 | Itoh et al. | 128/204.26 |
| 5,875,783 | A * | 3/1999 | Kullik | 128/204.18 |
| 6,176,208 | B1 * | 1/2001 | Tsuzuki et al. | 123/90.11 |
| 6,539,315 | B1 * | 3/2003 | Adams et al. | 702/47 |
| 2001/0035057 | A1 | 11/2001 | Jackson et al. | |

FOREIGN PATENT DOCUMENTS

| | | |
|---|---|---|
| DE | 31 38 985 A1 | 4/1983 |
| DE | 10044523 C2 | 4/2002 |
| DE | 10164234 A1 | 7/2003 |
| WO | WO 98/47425 | 10/1998 |

* cited by examiner

*Primary Examiner* — Louise Humphrey
(74) *Attorney, Agent, or Firm* — McGlew and Tuttle, P.C.

(57) ABSTRACT

A device for detecting the condition of flow in a respiration system combines the function of a nonreturn valve with the function of flow measurement in a common device. The device includes a valve arrangement (1) with a valve disk (9) and with a valve body (8), wherein the position of a valve disk (9) in relation to a valve seat (11) is detected. An indicator for a flow and a direction of flow (5), (6) is determined from the position of the valve disk (9). The position of the valve disk (9) can be determined inductively, electrically, electromechanically or optically. The flow and direction of flow (5), (6) determined can be used to control the respiration in a medical device.

20 Claims, 16 Drawing Sheets

DEVICE FOR DETERMINING A CONDITION OF FLOW IN A RESPIRATION SYSTEM

CROSS REFERENCE TO RELATED APPLICATIONS

This application claims the benefit of priority under 35 U.S.C. §119 of German Patent Application DE 10 2008 028 733.4 filed Jun. 17, 2008, the entire contents of which are incorporated herein by reference.

FIELD OF THE INVENTION

The present invention pertains to a device for recognizing oncoming flow effects at passively acting nonreturn valves. Determination of the volume flow, which is introduced into the patient, and of the quantity of breathing gas, which the patient again breathes out, is of considerable significance in the area of medical anesthesiology apparatus. For example, the absolute quantity of an anesthetic administered to a patient during anesthesia can be deduced from this. The absolute quantity of an anesthetic introduced is in turn a critical parameter in anesthesia, which should be known as exactly as possible. It is therefore important precisely in medical engineering to determine this variable as exactly as possible. It is just as decisive for this to be able to distinguish the phases of inspiration and expiration as precisely as possible.

BACKGROUND OF THE INVENTION

To avoid rebreathing by the patient, a nonreturn valve is inserted into the branch of the respirator that delivers the breathing gas to the patient. Breathing gas flows through this so-called inspiration branch in the rhythm of respiration during the phase of inspiration, and the nonreturn valve is opened during inspiration. The nonreturn valve closes the flow path during the phase of expiration. To determine the volume flows of inspiration and expiration, for example, flow sensors in the form of hot wire anemometers are known from the state of the art, which operate in such a way that the resistance of a hot wire, which is arranged in the breathing gas flow, is determined. The hot wire is made of a material that has a temperature-dependent resistance. The extent to which the hot wire is cooled by the gas flow depends on the volume flow and hence on the velocity of flow, so that the resistance of the hot wire is an indicator of the velocity of flow. One drawback of this process is, however, the fact that these hot wire sensors require a defined flow situation, which requires a certain section for homogenizing the flow and hence a certain overall length.

Both the flow sensors and the nonreturn valves are integrated with additional components, for example, a respiration drive and pressure sensors, in a respirator or anesthesia apparatus in a respiration system. This respiration system is designed such that it can be removed from the anesthesia apparatus for cleaning purposes. Due to the nonreturn valve and the flow sensor being arranged in series, a space requirement that essentially predefines the size of the entire respiration system is obtained in the respiration system. This makes it difficult to construct a compact respiration system.

SUMMARY OF THE INVENTION

The object of the present invention is to improve the functions of flow measurement and of the nonreturn valve in a compact embodiment. The essential advantage that the space requirement for the flow measurement and nonreturn valve can be reduced is obtained by the combination of the nonreturn valve and the flow sensor. Another advantage arises from the reduction of the number of elements in the respiration system, which reduces the susceptibility to error and improves maintenance friendliness.

The combination of flow measurement and nonreturn valve arises from the use of an element of the nonreturn valve to recognize the flow. In a passive nonreturn valve according to the state of the art, a disk is mounted on a number of holding elements or supports and seals the flow opening in case of planar contact in the valve seat. If only a flow from the side of the holding elements acts against the disk or there is a pressure gradient between the side of the holding elements and the opposite side of the disk, the disk is moved, so that the flow can pass through the valve. This is the direction of flow of the nonreturn valve. If the flow acts on the disk from the opposite side of the disk, the holding elements prevent a motion of the disk and no flow passes through the valve. This is the blocking direction of the nonreturn valve.

The motion of the disk is used in the present invention to recognize the flow of a gas.

A wound coil, which forms an electric oscillatory circuit together with a capacitor, is arranged as an inductance around the flow opening in a first embodiment according to the present invention. The oscillatory circuit has a natural frequency determined by the inductance and capacitance. The valve disk, which lies on the passage opening of the valve in the valve seat and seals same by contact and consists of a nondeformable material, for example, ceramic, is designed in this first embodiment according to the present invention such that an electrically conductive element with a relative magnetic permeability of about one is arranged as a valve element at or in the disk. The electrically conductive element determines, by its position in relation to the coil, an effect on the magnetic field by an eddy current being induced in the electrically conductive element.

The eddy current represents a load for the oscillatory circuit, which extracts energy from the oscillatory circuit. The value of the load depends on the position of the disk in relation to the coil. If the disk is moved away from the coil by the flow and hence also by the electrically conductive element, the eddy current losses in the magnetic-electric circuit of the device become lower. If the oscillatory circuit is excited from the outside by an electric a.c. voltage in the proximity of the natural frequency, the resulting amplitude of the oscillatory circuit can be analyzed as an indicator of the distance of the electrically conductive element from the coil and hence as an indicator of the amount of the motion of the disk by the flow. Thus, it is possible to distinguish phases of inspiration from phases of expiration as well as to quantitatively analyze the flow rate by means of a characteristic, which is plotted as a function of the change in amplitude per unit quantity passing through. The analysis of the position of the valve disk makes it possible to recognize the flow and the direction of flow. The flow and the direction of flow can be used to control the respiration in a medical device, for example, in a respirator or in an anesthesia apparatus.

An alternative variant of the first embodiment according to the present invention differs from this in that the valve disk is designed such that instead of an electrically conductive element, a magnetically conductive element with a relative magnetic permeability of >>1 is arranged as a valve element at or in the disk. As it were, an arrangement of a coil with a metal core and an air gap is thus obtained. The dimensions of the air gap are varied by the motion of the valve disk in the second embodiment according to the present invention.

The overall inductance of the array and hence, in cooperation with the capacitance, the natural frequency of the oscillatory circuit thus change due to the motion of the valve disk brought about by the flow in the direction of passage. If the oscillatory circuit is excited from the outside by an electrical a.c. voltage in the vicinity of the natural frequency, the resulting change in the Q factor of the oscillatory circuit is an indicator of the change in the air gap in the magnetic circuit and hence an indicator of the distance between the magnetically conductive element and the coil and can finally be analyzed as an indicator of the amount of motion of the disk by the flow.

The oscillatory circuit is preferably designed for the first embodiment such that the natural frequency is above the human hearing range of approx. 20 kHz; a value of 500 kHz is suitable as the upper limit value for the natural frequency to attain a sufficient depth of penetration of the magnetic field and to obtain a sufficient measuring effect.

In one variant of the first embodiment according to the present invention, the valve disk is held in an inoperative position by a prestressed mechanical spring element. The characteristic of the spring is selected to be such that the valve disk is raised by the flow against the spring force. The valve can be used in any desired installation position in such an arrangement, because the spring characteristic essentially determines the path and the position of the valve disk as a function of the flow.

In a preferred embodiment of the first embodiment according to the present invention, a disk made of a flexible material is fastened in the center of the passage opening on a holding structure. The holding structure is preferably of a star-shaped design and is fastened to the edge of the passage opening. The flexible valve disk is fastened in the center of the holding structure. The mode of operation arises from an elastic deformation and bending of the disk in the marginal area, as a result of which the air can pass through the valve from a direction of passage, the elastic deformation is restored into the original state without flow and again closes the valve by the contact surface of the valve disk not allowing any space for deformation in the valve seat, This arrangement with a valve disk made of a flexible material according to this preferred embodiment offers the advantage that the valve can operate in any desired installation position without an additional spring element, because the gravity acting on the valve disk is not utilized for sealing. The holding structure and the flexible valve disk are preferably designed such that the valve disk can be replaced by the user during cleaning and maintenance operations. A plurality of flexible plastics, elastomers or films, for example, neoprene or silicone, are available as the material for the valve disk for such a replacement part, because no specific requirements are imposed by single-time use on hygienic processing.

The closing of the valve is detected by a contact in a second embodiment according to the present invention. A flexible valve disk is fastened here eccentrically to a holding structure in the passage opening by means of at least one fastening point. A contact pair, which detects the closing of the valve, is arranged on the side located opposite the fastening side.

A valve seat is formed as a sealing closing surface for the valve in the outer contour of the passage opening.

The contact pair is designed as an electrical make contact pair in a preferred embodiment of the second embodiment according to the present invention. A contact bridge is arranged as a contacting element at or in the valve disk. At least one pair of electric contact elements, which is provided with electric feed lines, is arranged in the closing surface. With the valve closed, the pair of contact elements is electrically connected via the contact bridge and the resulting electrical connection can be detected by an electrical volume resistance or resistance measurement.

In an alternative variant of the embodiment according to the present invention, the contact pair is designed as an electromagnetic contact pair. An element made of a magnetic material is arranged here at or in the valve disk. An electromagnetic contact, preferably in the form of a Hall sensor or a Reed relay, which is provided with electrical feed lines, is arranged in the closing surface of the valve. With the valve closed, the electromagnetic element is actuated by the magnet in the valve disk, and the resulting electrical connection can be measured by an electrical volume resistance or resistance measurement.

In another embodiment variant, the contact pair is implemented by a contactless contact pair to detect the motion of the valve. A contactless contact pair can be implemented in the form of a photoelectric cell, where an array comprising a light source and a light receiver is arranged at the closing surface of the valve. For example, a light-emitting diode may be used as a light source, and photosensitive resistors, phototransistors or photodiodes may be used as light receivers.

With the valve closed, the optical path of the photoelectric cell is interrupted in a preferred embodiment by the valve disk and the signal of the light receiver is analyzed.

A preferred embodiment is designed such that the valve disk is introduced into the holding structure via at least two fastening points, the at least two fastening points being arranged asymmetrically and the shape of the valve disk being selected to be such that only an unambiguous possibility is available for fastening the valve disk in the holding structure. Incorrect installation position of the valve disk is thus ruled out.

A combination of the first embodiment with the second embodiment is provided in a third embodiment according to the present invention. A flexible valve disk is fastened here eccentrically at a holding structure in the passage opening by means of at least one fastening point. The valve disk is provided with a magnetically or electrically conductive material, whose approach to the valve seat can be detected via an arrangement in an oscillatory circuit according to the first exemplary embodiment. The analysis of the contact pair is used to determine a valve motion, which represents a final point in time of the phase of inspiration when the contact is closed and makes it possible to recognize breathing cycles, and the analysis of the change in the field is used for an additional quantitative evaluation of the flow rate over the determined opening path of the valve.

Exemplary embodiments of the present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 15c is a schematic top view of the detector of FIG. 15a; and

DESCRIPTION OF THE PREFERRED EMBODIMENTS

Figure 1:
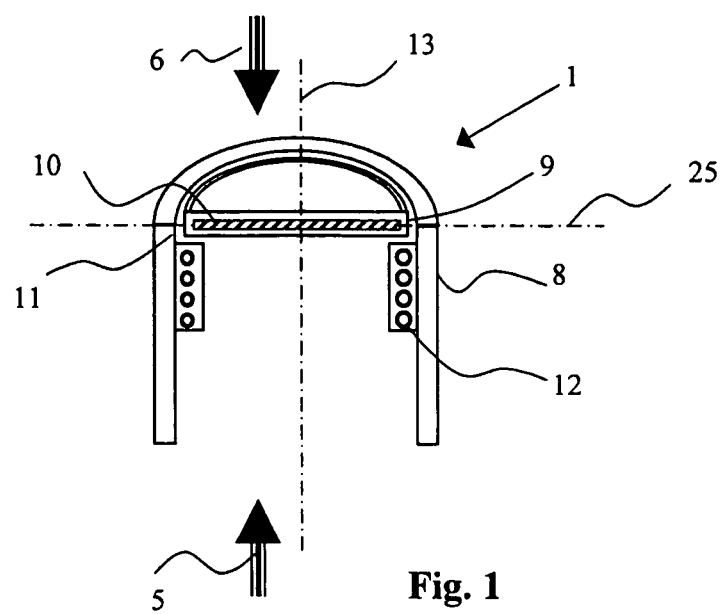
FIG. 1 is a schematic sectional view of a valve arrangement according to the invention with a nondeformable valve disk and a coil array.

Referring to the drawings in particular, FIG. 1 shows a schematic design of a first valve arrangement 1 according to the present invention in a half section along the horizontal axis 25 symmetrically to the central axis 13, which contains a round first valve disk 9 with a first valve element 10, designed as an embedded magnetic element, with a relative magnetic permeability substantially greater than one, a valve seat and a cylindrical valve body 8 with a coil 12 arranged thereon.

Figure 2:
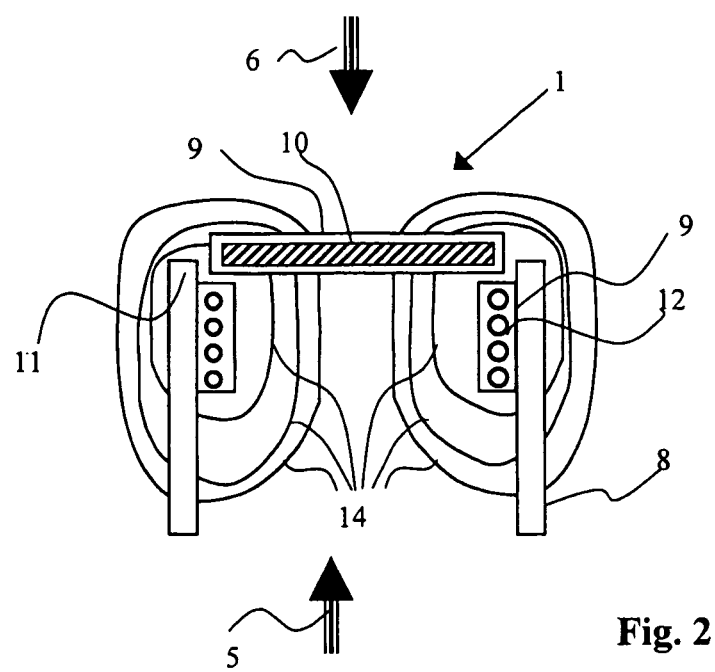
FIG. 2 is a schematic sectional view of the first valve arrangement according to FIG. 1 shown with a drawing of the lines of magnetic flux, in the closed state.

FIG. 2 shows the first valve arrangement 1 according to FIG. 1, wherein the first valve disk 9 with an embedded element 10 is sealingly seated on a first valve seat 11. The same reference numbers are used for identical components as in FIG. 1.

In addition, a first magnetic field line curve 14 is shown in the closed state of the first valve arrangement 1. The flow from the second direction of flow 6 cannot flow through the valve.

Figure 3:
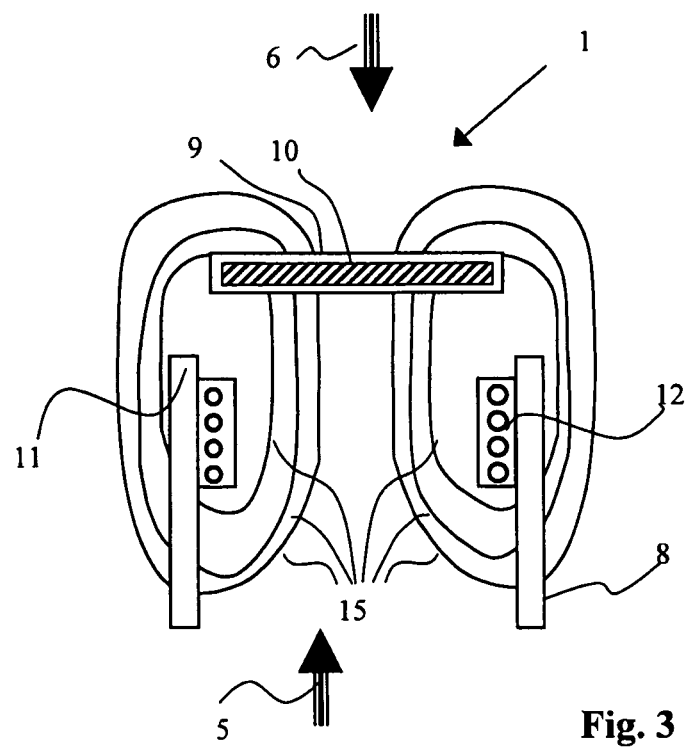
FIG. 3 is a schematic sectional view of the first valve arrangement according to FIG. 1 shown with a drawing of the lines of magnetic flux, in the opened state.

FIG. 3 shows the first valve disk 9 raised by the flow from the first direction of flow 5 and a second magnetic field line curve 15 in the opened state of the valve arrangement 1 according to FIG. 1. The same reference numbers are used for identical elements as in FIG. 1.

The different routing of the magnetic field lines 14, 15 with the opened and closed valve disk 9 can be seen in FIGS. 2 and 3.

Figure 4:
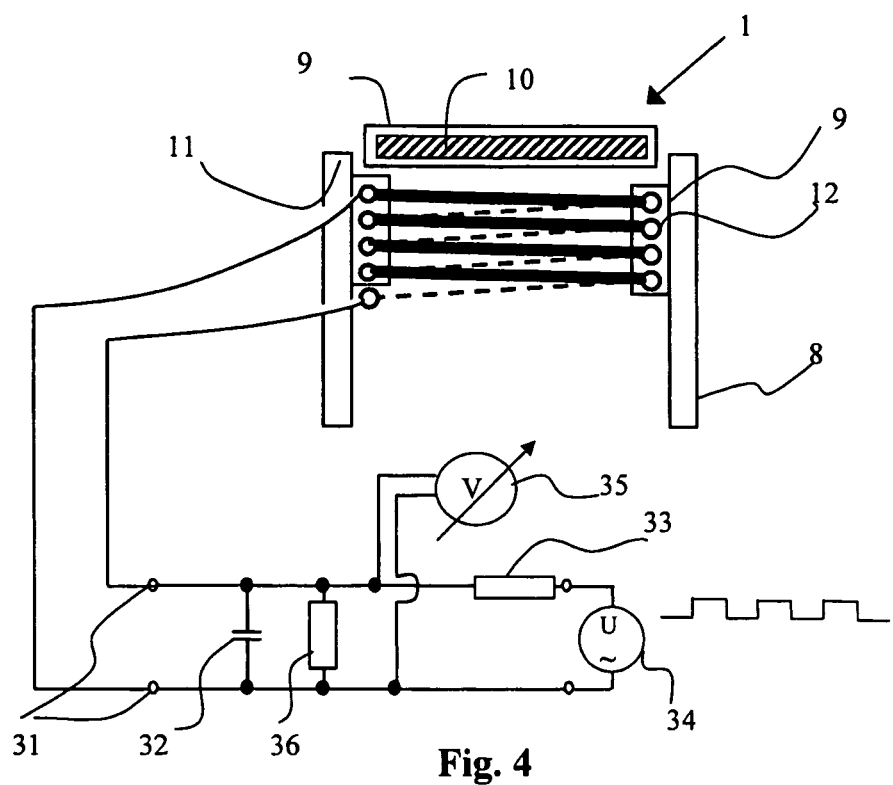
FIG. 4 is a schematic sectional view of an arrangement for the electrical analysis of the motions of the valve disk for the valves shown in FIGS. 1, 2 and 3.

FIG. 4 shows how the valve arrangement 1 according to the present invention as shown in FIGS. 1, 2 and 3 is integrated into an electronic circuit via a terminal contact pair 31. The same reference numbers are used for identical elements as in FIG. 1. The first valve disk 9 lies on a first valve seat 11. A first valve element 10 is embedded in the first valve disk 9. An operating electronic unit 30 contains an arrangement of a capacitor 32, which forms an electrical oscillatory circuit with a typical natural frequency together with the coil 12 located at the valve body 8. The parallel resistor 36 is designed suitably for setting the damping of the oscillatory circuit. The oscillatory circuit is excited to oscillate in the vicinity of its natural frequency by means of an a.c. voltage source 34 with a protective resistor 33. The first valve element 10 brings about damping of the amplitude of the oscillatory circuit, which is given by a proportional relationship with the distance between the first valve element 10 and coil 12. The amplitude of oscillation can be measured via a voltage-measuring device 35.

Figure 5:
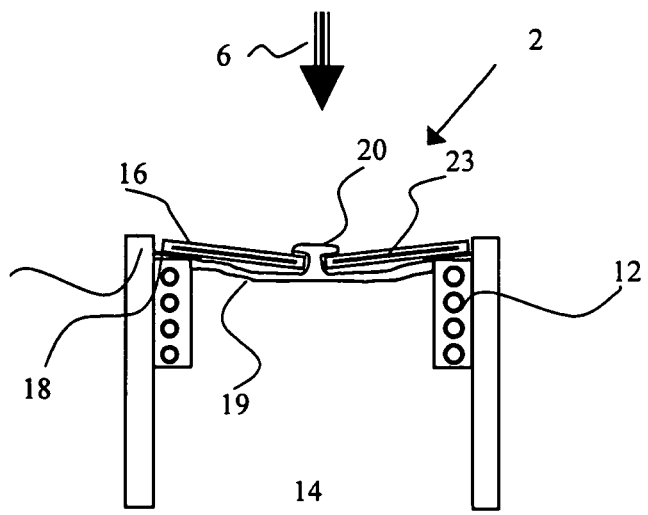
FIG. 5 is a schematic sectional view of a second valve arrangement with an elastic valve disk and a coil array, in the closed state.

FIG. 5 shows a second valve arrangement 2 with the peculiarity of an elastic second embodiment valve disk 16 and with a holding structure 19 for fastening the second embodiment valve disk 16.

The view shows the second embodiment valve disk 16 with a second embodiment valve element 23, designed as an embedded magnetic element with a relative magnetic permeability substantially greater than one, a second embodiment valve seat 18 and a cylindrical valve body 8 with a coil 12 arranged thereon. The second embodiment valve arrangement 2 is shown in the closed state. The second embodiment valve disk 16 with the second embodiment valve element 23 being fastened to the holding structure 19 is sealingly seated on the second embodiment valve seat 18, and flow according to the second direction of flow 6 is blocked in this manner.

Figure 6:
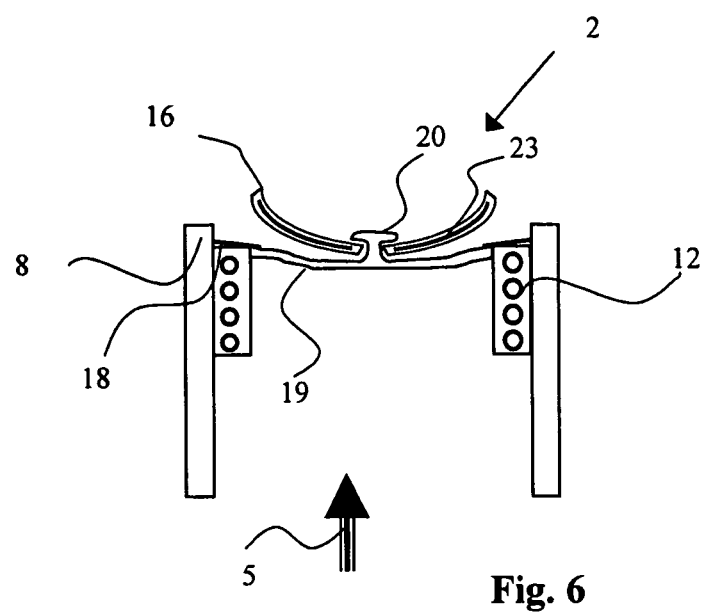
FIG. 6 is a schematic sectional view of the second valve arrangement according to FIG. 5, in the opened state.

FIG. 6 shows the second embodiment valve disk 16 raised by the flow from the first direction of flow in the opened state of the second embodiment valve arrangement 2 according to FIG. 5. The second embodiment valve disk 16 is raised by the flow at the edge from the second embodiment valve seat 18 because of the flexible design, the flow opening 7 (FIG. 7) is thus released, and the air can flow through the second embodiment valve arrangement 2 according to the first direction of flow 5.

Figure 7:
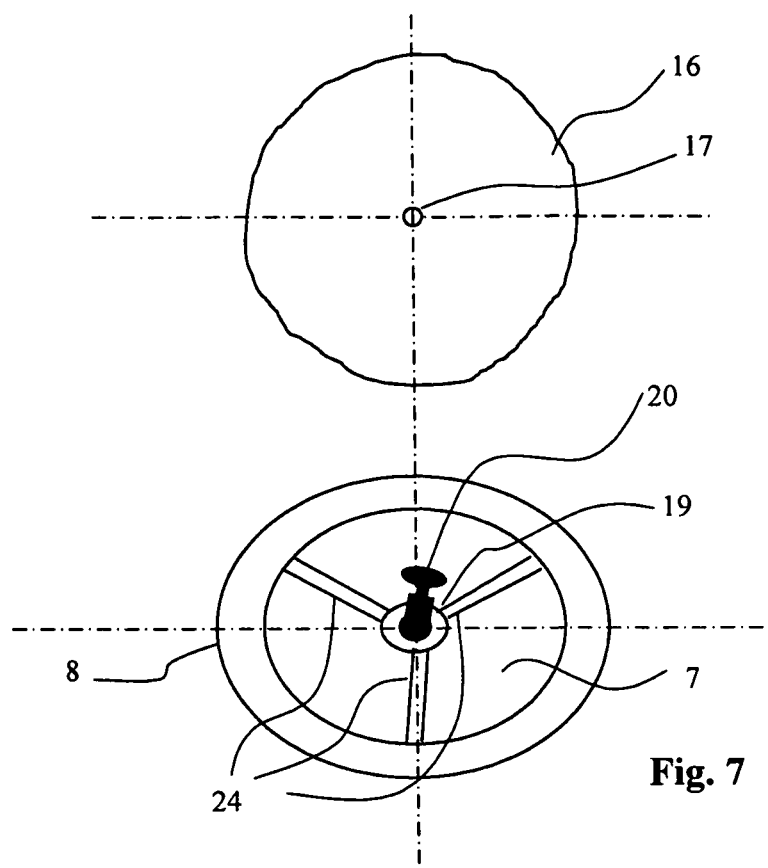
FIG. 7 is a schematic individual component exploded view of the elastic valve disk and of the holding structure of the second valve arrangement.

FIG. 7 shows a view of the second embodiment valve arrangement 2 according to FIGS. 5 and 6 comprising a second embodiment valve disk 16 and a holding structure 19 before joining together in a top view. The same reference numbers are used for identical elements as in FIG. 5. The holding structure 19 with a fastening point 20 receives the fastening hole 17 of the second embodiment valve disk 16. FIG. 7 also shows that the holding structure 19 leaves open a flow opening 7. The holding structure 20 is formed in this example in a cross-shaped pattern from three support struts 24 with central fastening point 20. Other shapes of the holding structure 19 can likewise be implemented.

Figure 8:
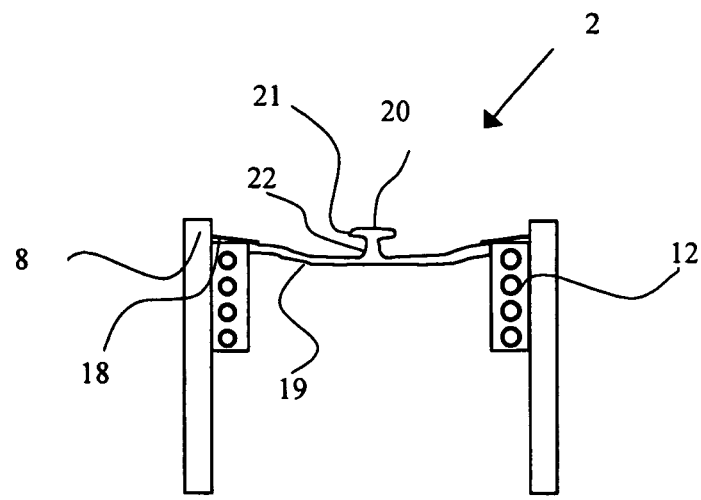
FIG. 8 is a schematic sectional side view of the holding structure of the second valve arrangement according to FIGS. 5 through 7.

FIG. 8 shows a side view of the holding structure 19 and the fastening point 20 in detail. The ratios of the dimensions of the fastening point 20 and the second embodiment valve disk 16 are decisive for the function of the second embodiment valve arrangement 16. The diameter of the fastening hole 17 of the second embodiment valve disk 16 is smaller than a cap 21 of the fastening point 20. The fastening diameter 22 of fastening point 20 is smaller than the diameter of fastening hole 17 (FIG. 7) of the second embodiment valve disk 16. The consequence of these dimension ratios is that the second embodiment valve disk 16 can be joined together with the fastening point 20 via cap 21 because of the elastic material, but it cannot be separated by the flow from the fastening point 20 any more beyond the cap 21 after joining. The second embodiment valve disk 16 is held with a sufficient tolerance at the fastening diameter 22 of fastening point 20 in order to be able to elastically follow the flow. This means for the application that before the use of the second embodiment valve arrangement 2, the second embodiment valve disk 16 is inserted into the holding structure 19 and can easily be removed after use, so that separate processing and disposal of the second embodiment valve disk 16 and of the valve body 8 is possible.

Figure 9:
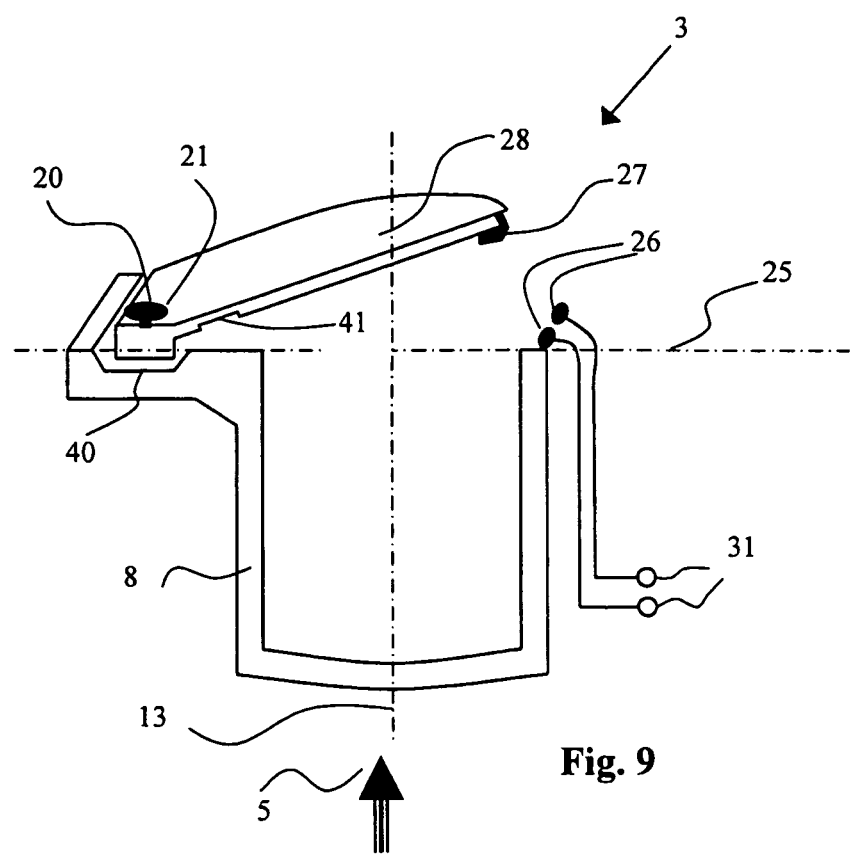
FIG. 9 is a schematic sectional view of a third valve arrangement with a valve disk and with a contact arrangement in the opened state.

FIG. 9 shows a third valve arrangement 3 in a half section along the horizontal axis 25 symmetrically to the central axis 15 with a third valve disk 28 and with a contact arrangement. The contact arrangement comprises electrical contact elements 26, which are electrically connected to one another in the inoperative state by an electrical contact bridge 27. The electrical contact is interrupted in the opened state shown of the third valve arrangement 3. The air flows through the third valve arrangement 3 according to the first direction of passage 5. The contact interruption can be contacted via the terminal contacts 31 and detected by an analysis circuit, not shown, for example, by means of a flow test or resistance measurement. The signal thus detected can be used as a trigger signal for controlling the respiration. The third valve disk 28 is connected by a mount 40 to the valve body 8. Fastening points 20 with a cap 21 keep the third valve disk 28 fixed laterally at the valve body 8. The third valve disk 28 is made thicker at the position of mount 40. A groove 41 is prepared in the third valve disk directly next to the mount 40, as a result of which the third valve disk 28 is mounted movably and elastically at the valve body 8 and can follow the flow motion.

Figure 10:
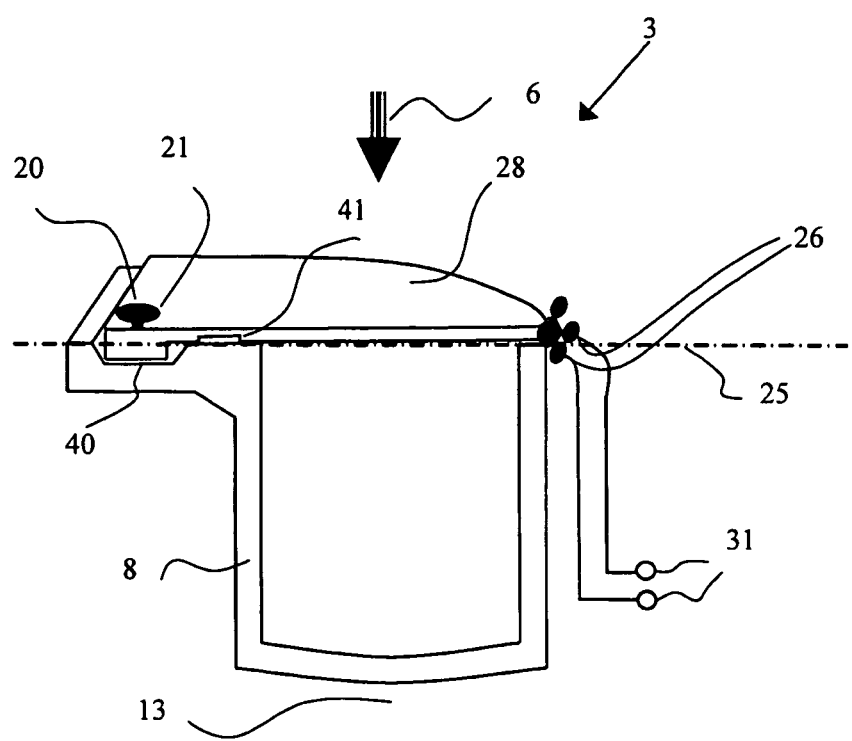
FIG. 10 is a schematic sectional view of the third valve arrangement according to FIG. 9, in the closed state.

FIG. 10 shows the third embodiment valve arrangement 3 according to FIG. 9 in the closed state. The same reference numbers are used for identical elements as in FIG. 9. Flow according to the second direction of flow 6 is blocked by the position of the third embodiment valve disk 28. The contact connection can be contacted via the terminal contacts 31 and detected by an analyzing circuit, not shown, for example, by means of a flow test or resistance measurement. The signal detected in the process can be used as a trigger signal for controlling respiration in a respirator.

Figure 11:
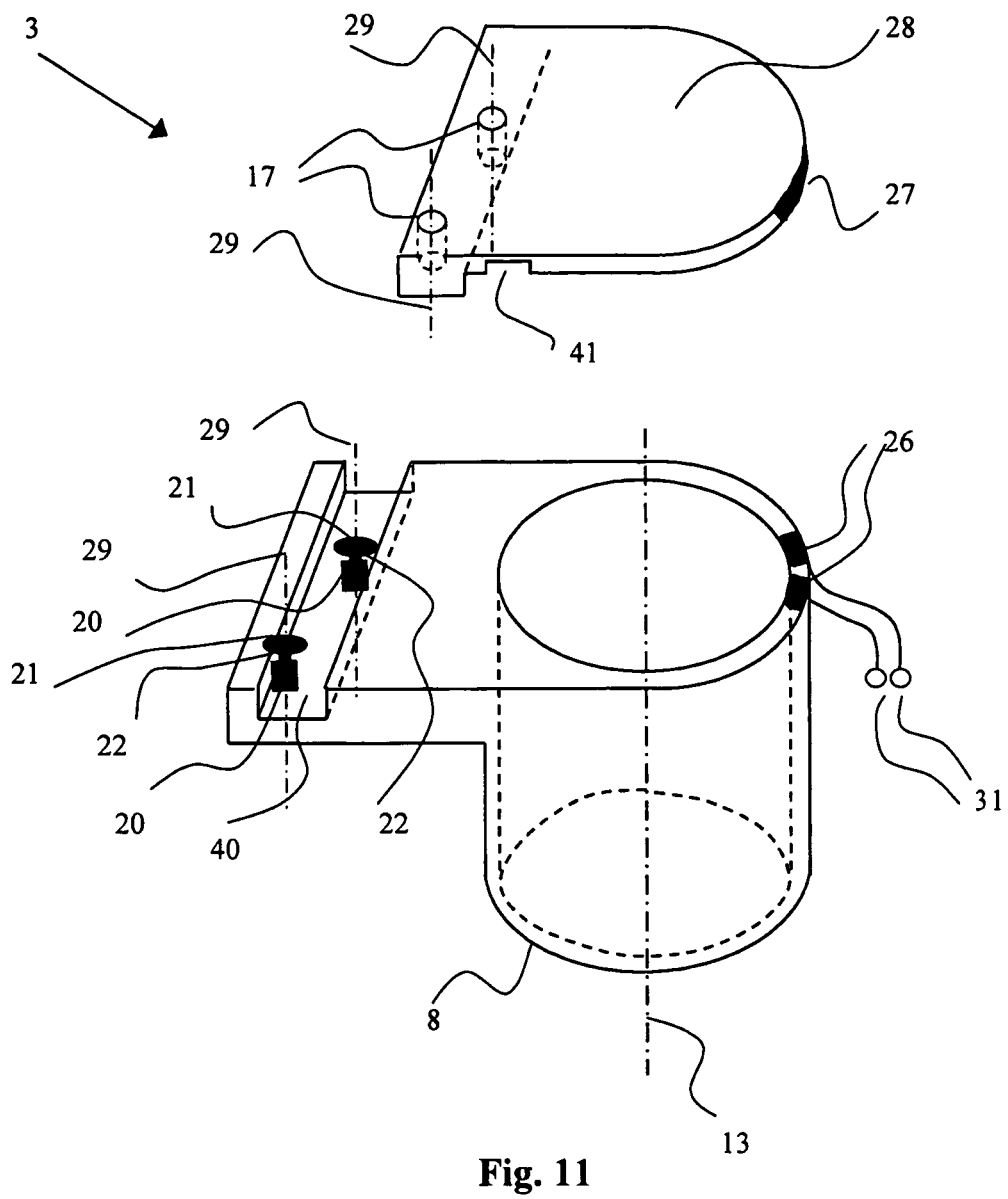
FIG. 11 is a schematic individual component exploded view of the third valve disk and of the valve body of the third valve arrangement.

FIG. 11 shows a view of the third embodiment valve arrangement 3 comprising the third embodiment valve disk 28 and a cylindrical valve body symmetrical to the central axis according to FIGS. 9 and 10 before joining together in a three-dimensional view. The same reference numbers are used for identical elements as in FIGS. 10 and 11. The fastening points 26 in mount 40 at the valve body receive the fastening holes 17 of valve disk 28.

The ratios of the dimensions of the fastening points 20 and the third embodiment valve disk 28 are decisive for the function of the third embodiment valve arrangement 3. The diameter of the fastening holes 17 of the third embodiment valve disk 28 is smaller than the caps 21 of the fastening points 20. The fastening diameter 22 of the fastening points 20 is made smaller than the diameters of the fastening holes 17 of the third embodiment valve disk 28. The consequence of these ratios of the dimensions is that the third embodiment valve disk 28 can be joined together with the fastening points via the caps 21 because of the elastic material, but it cannot be separated from the fastening points any more by the flow beyond the cap 21 after joining. The third embodiment valve disk 28 is held with sufficient tolerance at the fastening diameters 22 of the fastening points 20 in order to be able to elastically follow the flow. For use in the application, this means that the third embodiment valve disk 28 is inserted into the valve body 8 before the third embodiment valve arrangement 3 is used and it can be easily removed after use, so that separate processing or disposal of the third embodiment valve disk 28 and of the valve body 8 is possible.

The third embodiment valve disk 28 is introduced into mount 40 via two fastening points 20, wherein fastening points 20 are arranged in the valve body 8 asymmetrically on two fastening axes 29 offset at right angles, and the shape of the third embodiment valve disk 28 is selected to be such that only an ambiguous possibility is possible for fastening the valve disk 28 at the valve body 8. Incorrect assembly is thus ruled out. Unambiguity is additionally predetermined by the asymmetry of the fastening points 20 in conjunction with mount 40, combined with the shape of the valve disk 28, which is half-round on one side and rectangular.

Figure 12:
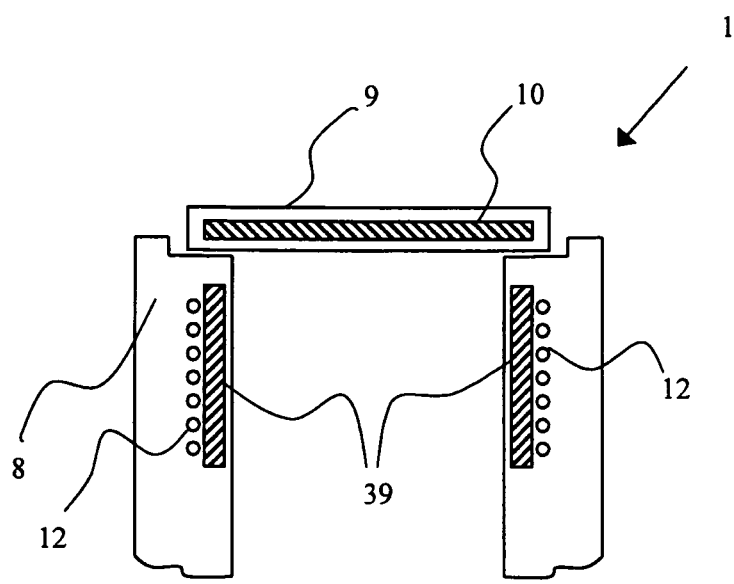
FIG. 12 is a schematic sectional view of a variant of the first valve arrangement.

FIG. 12 shows a first valve arrangement 1 according to FIG. 1 comprising a valve disk 9 with an embedded valve element 10 and a coil 12 with a metal element arranged additionally at the valve body 8. The same reference numbers are used for identical elements as in FIG. 1. The metal element 39 brings about guiding of the magnetic field lines and thus intensifies the measuring effect, which is caused by the motion of the first valve disk 9.

Figure 13:
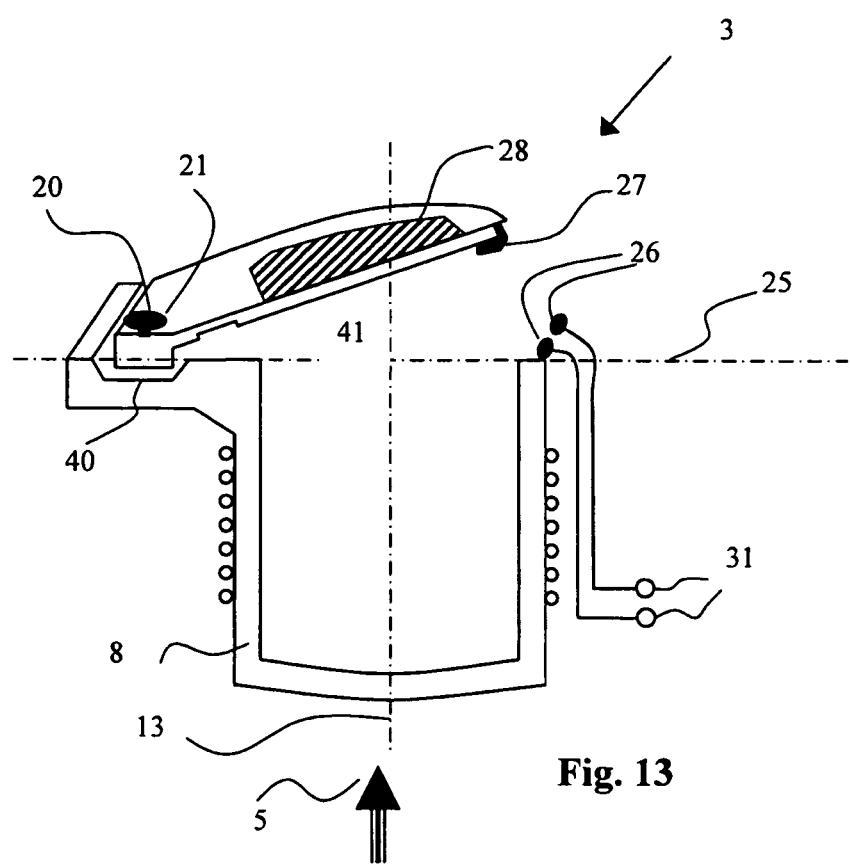
FIG. 13 is a schematic sectional view of a variant of the third valve arrangement.

FIG. 13 shows a variant of the third arrangement according to FIG. 9. The same reference numbers are used for identical elements as in FIG. 9 and FIG. 1.

A coil 12 and a valve element 10 with a contact arrangement, comprising electrical contact elements 26 and an electrical contact bridge 27, are arranged at the valve body 8 in this variant. Analysis of the contact connection can be used in this variant to recognize the phase of breathing, for example, to trigger a respirator. The position of valve element 10 in or at the third embodiment valve disk 28 in relation to the coil arranged around the coil form does affect the properties of the magnetic field.

The change in the magnetic field properties is analyzed by means of an operating electronic unit (FIG. 4) and it yields a quantitative indicator of flow as an additional measured variable besides the recognition of the phase of breathing.

Figure 14:
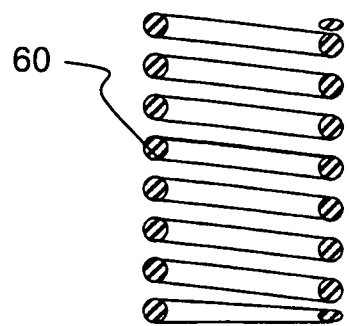
FIG. 14 is a sectional view of a spring element for holding the valve disk in an inoperative position with a spring bias.

In a variant of the first embodiment according to the present invention, the valve disk is held in an inoperative position by a prestressed mechanical spring element 60 as shown in FIG. 14. The characteristic of the spring 60 is selected to be such that the valve disk is raised by the flow against the spring force. The valve can be used in any desired installation position in such an arrangement, because the spring characteristic essentially determines the path and the position of the valve disk as a function of the flow.

Figure 15A:
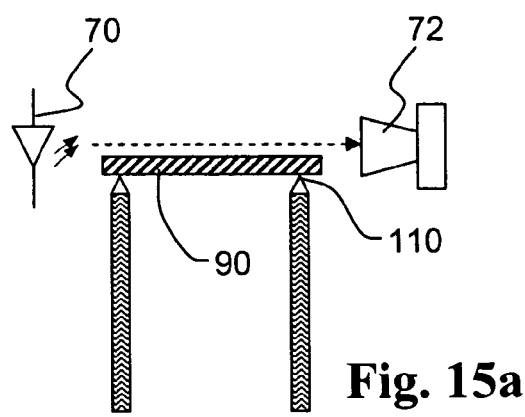
FIG. 15a is a schematic view of a detector including a photoelectric cell with LED and receiver for the optical detection of the position of a valve disk, with the valve disk shown seated.
Figure 15B:
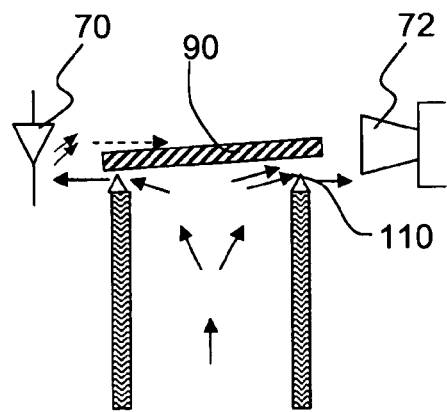
FIG. 15b is a schematic view of the detector of FIG. 15a, with the valve disk shown unseated.
Figure 15C:
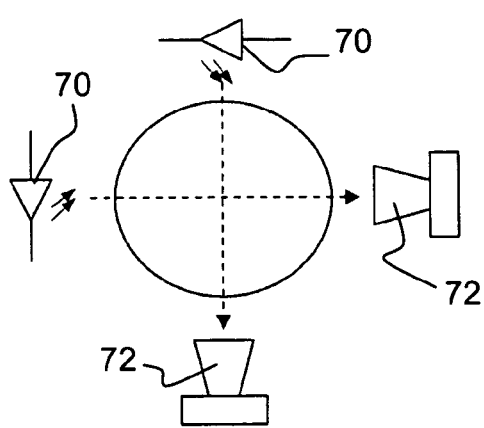

FIGS. 15a, 15b and 15c shows features in which the detector comprises a photoelectric cell with LED 70 and receiver 72 for the optical detection of the position of a valve disk 90 in relation to the valve seat 110. With the valve closed (FIG. 15a), the optical path of the photoelectric cell is uninterrupted by the valve disk 90. With valve open (FIG. 15b), the optical path of the photoelectric cell is interrupted by the valve disk and the signal of the light receiver is analyzed. The situation may be reversed such that with the valve closed the optical path of the photoelectric cell is interrupted. As shown in FIG. 15c, the detector preferably provides two directions of measurement with photoelectric cells to provide two LEDs 70 and two receivers 72.

Figure 16:
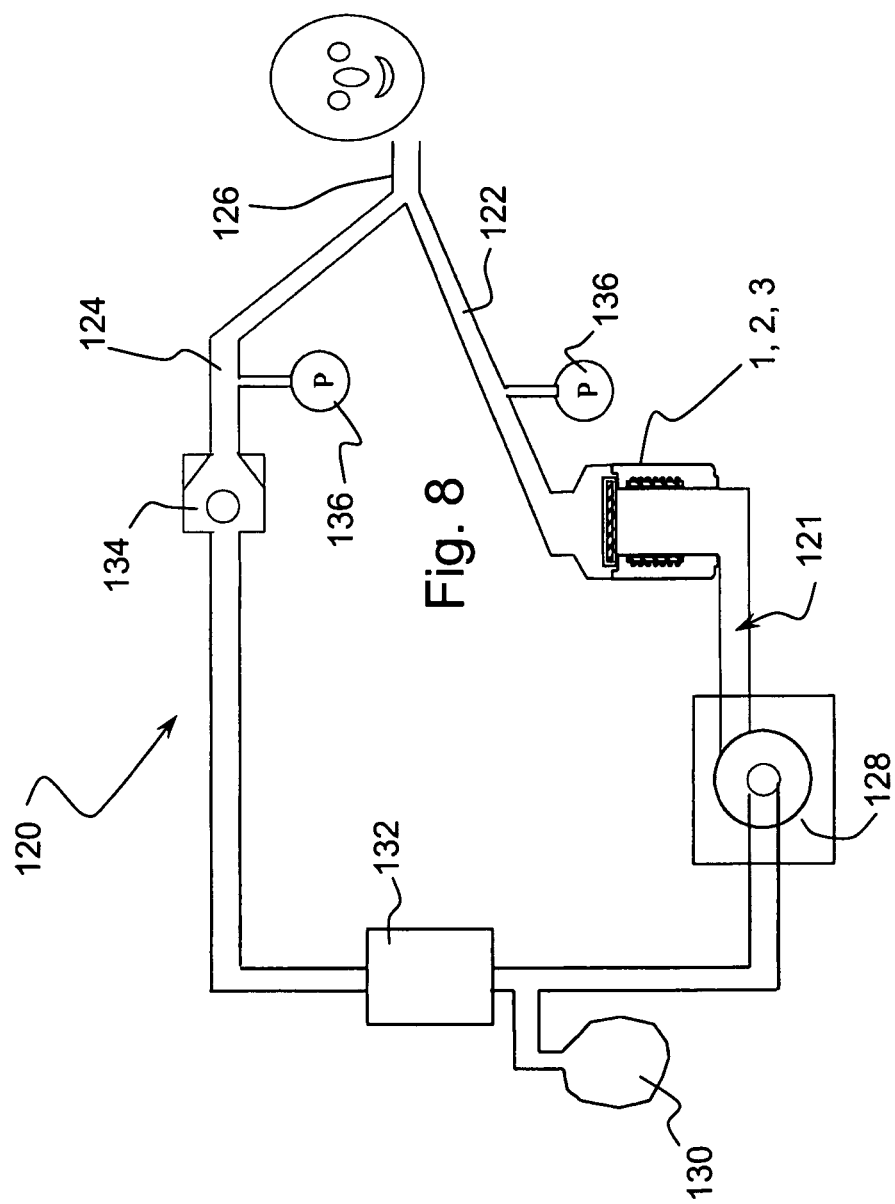
FIG. 16 is a schematic view of a respiration system with a valve arrangement according to the invention.

FIG. 16 shows a respiration system 120 with a respiration breathing gas flow passage 121 including an inspiration branch 122 and an expiration branch 124 with a patient connection 126. The device 1, 2, 3 is provided for determining a flow condition in the breathing gas flow passage 121 of the respiration system. The respiration system 120 may include a blower/compressor 128 and may be a closed loop as shown with buffer volume 130 and $CO_2$ absorber 132 and directional valve 134. Other respiration system arrangements are also possible including respirator/ventilator systems which dispense anesthetic.

While specific embodiments of the invention have been shown and described in detail to illustrate the application of the principles of the invention, it will be understood that the invention may be embodied otherwise without departing from such principles.

Appendix:
List of Reference Numbers

| List of Reference Numbers | |
|---|---|
| 1 | First valve arrangement |
| 2 | Second valve arrangement |
| 3 | Third valve arrangement |
| 4 | Fourth valve arrangement |
| 5 | First direction of flow |
| 6 | Second direction of flow |
| 7 | Passage opening |
| 8 | Valve body |
| 9 | First valve disk |
| 10 | First valve element |
| 11 | First valve seat |
| 12 | Coil |
| 13 | Central axis |
| 14 | First magnetic field line curve |
| 15 | Second magnetic field line curve |
| 16 | Second valve disk |
| 17 | Fastening hole |
| 18 | Second valve seat |
| 19 | Holding structure |
| 20 | Fastening point |
| 21 | Cap |
| 22 | Fastening diameter |
| 23 | Second valve element |
| 24 | Support strut |
| 25 | Horizontal axis |
| 26 | Contact elements |
| 27 | Contact bridge |
| 28 | Third valve disk |
| 29 | Fastening axis |
| 30 | Operating electronic unit |
| 31 | Terminal contact pair |
| 32 | Capacitor |
| 33 | Protective resistor |
| 34 | A.c. voltage source |
| 35 | Voltage measuring device |
| 36 | Parallel resistor |
| 39 | Metal element |
| 40 | Mount |
| 41 | Groove |

What is claimed is:

1. A device for determining a flow condition in a respiration system, the device comprising:
a valve arrangement with a valve disk and with a valve body with a valve seat, the valve disk being connected to the valve body to define a nonreturn valve with flow passing through the nonreturn valve in a flow direction of the nonreturn valve with movement of a portion of said valve disk relative to the valve seat by a distance that is a function of a flow quantity through the valve arrangement and blocking flow through the nonreturn valve in a flow blocking direction with the valve disk seated on the valve seat;
a fluid flow quantity detector comprising:
a magnetic element arranged in or at the valve disk, the magnetic element comprising at least one of magnetically conductive material with a relative magnetic permeability substantially greater than one and a magnetic material; and
a magnetic element position detector comprising at least one of a coil arranged at said valve body for an inductive detection of a position of said valve disk in relation to said valve seat and a Reed relay or Hall sensor arranged at said valve body for an electromagnetic detection of a position of said valve disk in relation to said valve seat;
a fluid flow direction detector comprising a contact element on one of said valve element and said valve seat and contact makers on another of said valve element and said valve seat for electrically detecting a position of said valve disk in relation to said valve seat whereby a direction of flow is determined based on whether the valve disk is seated on the valve seat or not; and
an indicator for indicating a flow quantity and a direction of flow from the position of said valve disk in relation to said valve seat detected by said fluid flow quantity detector and said fluid flow direction detector.

2. A device in accordance with claim 1, wherein the position of said valve disk is determined by detecting a change in a circuit comprising said coil and said magnetically conductive material.

3. A device in accordance with claim 2, further comprising an electrically excited oscillatory circuit for detecting changes in the circuit.

4. A device in accordance with claim 1, wherein said detector further comprises a photoelectric cell for the optical detection of the position of a valve disk in relation to the valve seat.

5. A device in accordance with claim 1, wherein said valve disk is made of a nondeformable material.

6. A device in accordance with claim 1, wherein said valve disk is made of a flexible material.

7. A device in accordance with claim 1, wherein said valve disk and the connection of said valve disk to said valve body form a flow reaction device including a mechanical disk biasing means for biasing said valve disk toward a seated position with said valve disk seated on said valve seat and providing a relationship between the movement of the portion of said valve disk relative to the valve seat and the flow quantity through the valve arrangement.

8. A device in accordance with claim 7, wherein said mechanical disk biasing means comprises a prestressed mechanical spring biasing said valve disk toward a seated position with said valve disk seated on said valve seat and in part determining a relationship between the movement of the portion of said valve disk relative to the valve seat and the flow quantity through the valve arrangement.

9. A device in accordance with claim 7, wherein said mechanical disk biasing means comprises material of the valve disk biasing said valve disk toward a seated position with said valve disk seated on said valve seat and in part determining a relationship between the movement of the portion of said valve disk relative to the valve seat and the flow quantity through the valve arrangement.

10. A device in accordance with claim 1, wherein said valve disk is separably connected to said valve body via fastening points.

11. A device in accordance with claim 1, wherein the valve body has at least two fastening points displaced in relation to one another along a fastening axes and a mount in the valve body for unambiguously determining a connection of said valve disk to said valve body.

12. A device in accordance with claim 1, wherein said valve disk is provided with a groove to increase mobility of said valve disk.

13. A device in accordance with claim 1, wherein said indicator for indicating a flow quantity and a direction of flow forms control signals for controlling respiration in a medical device.

14. A device in accordance with claim 1, wherein;
said valve disk is operatively connected to said valve body to form a flow reaction surface positioned to be acted on by breathing gas flow such that at least a portion of said valve disk moves away from said valve seat for breathing gas flow in the flow direction and a degree of movement, of said at least a portion of said valve disk, away from said valve seat in the flow direction is dependent on a rate of flow through said valve arrangement past said valve disk; and
said arrangement of contact elements detecting a position of said valve disk in relation to said valve seat detects contact of said valve disk with said valve seat as an indication of direction of flow.

15. A respiration system comprising:
a respiration breathing gas flow passage including an inspiration branch and an expiration branch with a patient connection; and
a device for determining a flow condition in the breathing gas flow passage of the respiration system, the device comprising
  a nonreturn valve arrangement with a valve disk and with a valve body with a valve seat, said valve disk being connected to said valve disk to define a flow reaction device responsive to a breathing gas flow with at least a portion of said valve disk moving away from said valve seat for breathing gas flow in a flow direction of flow and with a degree of movement of said at least a portion of said valve disk away from said valve seat being dependent on a rate of flow through said nonreturn valve arrangement past said valve disk and with said valve disk being pressed by breathing gas flow in a flow blocking direction into contact with said valve seat to prevent fluid flow through said nonreturn valve arrangement past said valve disk in said flow blocking direction of the nonreturn valve arrangement, whereby said nonreturn valve arrangement allows breathing gas flow in the flow direction and prevents breathing gas flow in the blocking direction,
  a fluid flow quantity detector comprising:
    a magnetic element arranged in or at the valve disk, the magnetic element comprising at least one of magnetically conductive material with a relative magnetic permeability substantially greater than one and a magnetic material;
    a magnetic element position detector comprising at least one of a coil arranged at said valve body for an inductive detection of a position of said valve disk in relation to said valve seat and a Reed relay or Hall sensor arranged at said valve body for an electromagnetic detection of a position of said valve disk in relation to said valve seat;
  a fluid flow direction detector comprising a contact element on one of said valve element and said valve seat and contact makers on another of said valve element and said valve seat for electrically detecting a position of said valve disk in relation to said valve seat whereby a direction of flow is determined based on whether the valve disk is seated on the valve seat or not; and
  an indicator for indicating a flow quantity and a direction of flow from the position of said valve disk in relation to said valve seat detected by said fluid flow quantity detector and said fluid flow direction detector.

16. A respiration system in accordance with claim 15, wherein the position of said valve disk is determined by detecting a change in an electrically excited oscillatory circuit comprising said coil and said magnetically conductive material.

17. A respiration system in accordance with claim 15, wherein said flow reaction device further comprises a mechanical disk biasing means for biasing said valve disk toward a seated position with said valve disk seated on said valve seat and setting the degree of movement of the portion of said valve disk in relation to the rate of flow through said nonreturn valve arrangement.

18. A device for determining a flow condition in a respiration system, the device comprising:
  a nonreturn valve arrangement comprising a valve body with a valve seat and a valve disk, said valve disk being operatively connected to said valve body to form a flow reaction device reacting to a breathing gas flow by moving relative to said valve seat such that a portion of said valve disk moves a distance away from said valve seat, with breathing gas flow in a flow direction, with the distance moved being a function of the rate of flow through said nonreturn valve arrangement, and blocking flow through the nonreturn valve arrangement in a flow blocking direction with the valve disk seated on the valve seat;
  a fluid flow quantity detector comprising:
    a magnetic element arranged in or at the valve disk, the magnetic element comprising at least one of magnetically conductive material with a relative magnetic permeability substantially greater than one and a magnetic material; and
    a magnetic element position detector comprising at least one of a coil arranged at said valve body for an inductive detection of a position of said valve disk in relation to said valve seat and a Reed relay or Hall sensor arranged at said valve body for an electromagnetic detection of a position of said valve disk in relation to said valve seat;
  a fluid flow direction detector comprising a contact element on one of said valve element and said valve seat and contact makers on another of said valve element and said valve seat for electrically detecting a position of said valve disk in relation to said valve seat whereby a direction of flow is determined based on whether the valve disk is seated on the valve seat or not; and
  an indicator for indicating a flow quantity and a direction of flow from the position of said valve disk in relation to said valve seat detected by said fluid flow quantity detector and said fluid flow direction detector.

19. A device in accordance with claim 18, wherein said connection of said valve disk to said valve body to form said flow reaction device comprises a mechanical biasing device biasing said valve disk against said valve seat and with a bias force characteristic of said mechanical biasing device contributing to the function of the rate of flow in relation to the distance of the valve disk away from said valve seat.

20. A device in accordance with claim 18, wherein said indicator for indicating a flow quantity and a direction of flow forms control signals for controlling respiration in a medical device.

* * * * *